(12) United States Patent
Thorson et al.

(10) Patent No.: US 8,637,287 B2
(45) Date of Patent: Jan. 28, 2014

(54) GLYCOSYLTRANSFERASE REVERSIBILITY FOR SUGAR NUCLEOTIDE SYNTHESIS

(75) Inventors: Jon S. Thorson, Middleton, WI (US); Richard W. Gantt, Roswell, GA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 192 days.

(21) Appl. No.: 13/159,097

(22) Filed: Jun. 13, 2011

(65) Prior Publication Data

US 2011/0306074 A1 Dec. 15, 2011

Related U.S. Application Data

(60) Provisional application No. 61/354,037, filed on Jun. 11, 2010.

(51) Int. Cl.
*C12N 9/10* (2006.01)
*C12N 1/00* (2006.01)

(52) U.S. Cl.
USPC .......................................... 435/193; 435/183

(58) Field of Classification Search
None
See application file for complete search history.

(56) References Cited

PUBLICATIONS

Yang et al., Journal of American Chemical Society vol. 127, pp. 9336-9337, 2005.*
Ngo et al. in The Protein Folding Problem and Tertiary Structure Prediction, 1994, Merz et al. (ed.), Birkhauser, Boston, MA, pp. 433 and 492-495.*
Lairson LL, et al. "Mechanistic analogies amongst carbohydrate modifying enzymes" (2004) Chem Commun 2243-8.
Hu, Y., et al. "Remarkable structural similarities between diverse glycosyltransferases" (2002) Chem Biol 9: 1287-96.
Hancock, SM, et al. "Engineering of glycosidases and glycosyltransferases" (2006) Curr Opin Chem Biol 10: 509-19.
Hoffmeister D, et al. "Creation of the first anomeric D/L-sugar kinase by means of directed evolution" (2003) Proc Natl Acad Sci U S A 100: 13184-9.
Williams, GJ, et al. "Creation of a pair of stereochemically complementary biocatalysts" (2006) J Am Chem Soc 128: 16238-47.

* cited by examiner

*Primary Examiner* — Richard Hutson
(74) *Attorney, Agent, or Firm* — Quarles & Brady LLP

(57) ABSTRACT

The present invention generally relates to materials and methods for exploiting glycosyltransferase reversibility for nucleotide diphosphate (NDP) sugar synthesis. The present invention provides engineered glycosyltransferase enzymes characterized by improved reaction reversibility and expanded sugar donor specificity as compared to corresponding non-mutated glycosyltransferase enzymes. Such reagents provide advantageous routes to NDP sugars for subsequent use in a variety of biomedical applications, including enzymatic and chemoenzymatic glycorandomization.

2 Claims, 13 Drawing Sheets

GLYCOSYLTRANSFERASE REVERSIBILITY FOR SUGAR NUCLEOTIDE SYNTHESIS

CROSS-REFERENCE TO RELATED APPLICATIONS

This application claims the benefit of U.S. Provisional Application No. 61/354,037, filed Jun. 11, 2010, the entirety of which is hereby incorporated by reference for all purposes.

STATEMENT RELATED TO FEDERAL FUNDING

This invention was made with government support under Grant No. AI052218, awarded by the National Institutes of Health. The government has certain rights in the invention.

FIELD OF THE INVENTION

This invention relates generally to the fields of glycobiology and the synthesis of glycosylated compounds. In particular, the present invention encompasses materials and methods for exploiting glycosyltransferase reversibility to provide nucleotide diphosphate (NDP) sugar synthesis.

BACKGROUND OF THE INVENTION

Glycosyltransferases (GTs) constitute a large family with approximately 23,000 predicted or known GT sequences in the CAZY database divided into 87 families based upon amino acid similarity. Despite the vast range of GT sugar donors and acceptors (sugars, proteins, nucleic acids, lipids, and small molecules), GTs are generally classified into two simple groups based upon mechanism (inverting or retaining), and primarily fall within two main structural superfamilies (GT-A and GT-B). Lairson L L, et al. (2004) *Chem Commun* 2243-8; Hu Y., et al. (2002) *Chem Biol* 9: 1287-96. The GT-B fold is the predominate fold of natural product GTs and is characterized by two closely associated Rossman-like domains, each of which is usually distinguished as the acceptor- and donor-binding domains (N and C-terminal domains, respectively). Despite the wealth of GT structural and biochemical information, attempts to alter GT donor/acceptor specificities via rational engineering have been largely unsuccessful and primarily limited to sequence-guided single site mutagenesis. Hancock S M, et al. (2006) *Curr Opin Chem Biol* 10: 509-19. While there exists precedent for the directed evolution of carbohydrate-utilizing enzymes, the lack of sensitive high-throughput screens for GTs has also hampered GT directed evolution. Hoffmeister D, et al. (2003) *Proc Natl Acad Sci USA* 100: 13184-9; Williams G J, et al. (2006) *J Am Chem Soc* 128: 16238-47.

Nucleotide diphosphate (NDP) sugars are common substrates for GTs where they routinely act as glycoside donors. A generic structure for an NDP sugar is depicted in FIG. 1. In general, NDP sugars represent a class of compounds routinely utilized in the investigation of polysaccharide formation for basic metabolism, intra- and extracellular transport, cell wall biosynthesis within virulent organisms, and drug discovery. However, synthesis of sugar-nucleotides is currently expensive, difficult and time-consuming, and is further complicated by their low solubility in organic solvents and susceptibility to both chemical and enzymatic hydrolysis. Further, an exemplary GT reaction utilizing an NDP sugar, in this case GtfD, is shown in FIG. 2.

While classical synthetic strategies to access sugar nucleotides are available, most require many steps and often suffer from low-yielding reactions, difficult purifications, and a lack of stereochemical control. Accordingly, a need exists for new reagents and routes to provide NDP sugars for a variety of uses in the biomedical field.

SUMMARY OF THE INVENTION

The present invention relates to novel glycosyltransferases and improved methods of NDP-sugar synthesis. Applications for this novel method include efficient synthesis of NDP-sugars with complete stereochemical control, in vitro formation for drug discovery, and robust microscale glycosyl scanning for assessing large compound libraries.

Accordingly, the invention provides in a first aspect an isolated mutant glycosyltransferase comprising: (a) the amino acid sequence of OleD glycosyltransferase set forth in SEQ ID NO:1, wherein proline at position 67 has been replaced with threonine, serine at position 132 has been replaced with phenylalanine, alanine at position 242 has been replaced with leucine, and glutamine at position 268 has been replaced with valine; or (b) an amino acid sequence substantially identical to OleD glycosyltransferase (SEQ ID NO:1) in which proline at position 67 has been replaced with threonine, serine at position 132 has been replaced with phenylalanine, alanine at position 242 has been replaced with leucine, and glutamine at position 268 has been replaced with valine; wherein the isolated mutant exhibits an improved conversion of nucleotide diphosphate (NDP) to NDP sugar as compared to a corresponding non-mutated glycosyltransferase. In preferred embodiments, the isolated mutant glycosyltransferase is encoded by a nucleotide that hybridizes under stringent conditions to the nucleotide sequence set forth in SEQ ID NO:2.

In a second aspect, the invention provides a method of providing an isolated mutant glycosyltransferase with improved conversion of nucleotide diphosphate (NDP) to NDP sugar as compared to a corresponding non-mutated glycosyltransferase. Such a method includes steps of: (a) mutating an isolated nucleic acid sequence encoding an amino acid sequence identical to or substantially identical to OleD glycosyltransferase (SEQ ID NO:1) in which proline at position 67 has been replaced with threonine, serine at position 132 has been replaced with phenylalanine, alanine at position 242 has been replaced with leucine, and glutamine at position 268 has been replaced with valine; (b) expressing said isolated nucleic acid in a host cell; and (c) isolating from the host cell a mutant glycosyltransferase that is characterized by improved conversion of nucleotide diphosphate (NDP) to NDP sugar as compared to a corresponding non-mutated glycosyltransferase.

In another aspect, the invention encompasses a method of providing a nucleotide diphosphate (NDP) sugar. Such a method includes steps of incubating a nucleotide diphosphate and a glycoside donor in the presence of an isolated mutant glycosyltransferase described and claimed herein to provide an NDP sugar.

In certain methods, the glycoside donor has the structure:

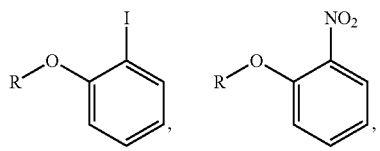

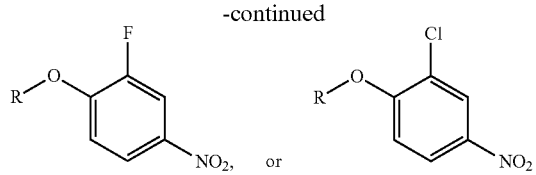

wherein R is β-D-glucopyranose.

In other embodiments, the glycoside donor has the structure:

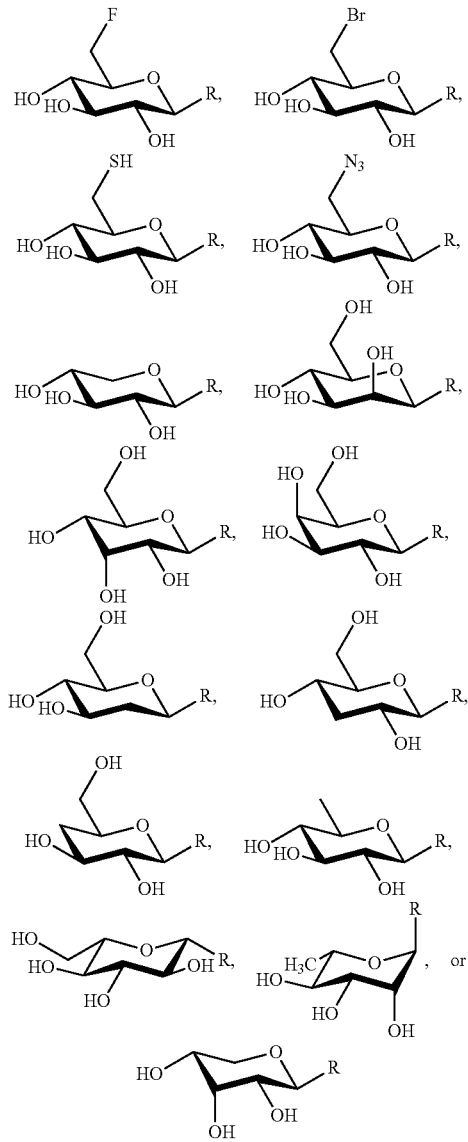

wherein R is:

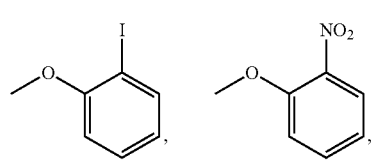

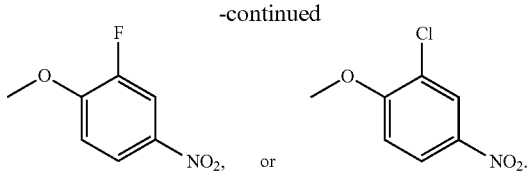

The NDP is preferably uridine or thymidine diphosphate. In alternative embodiments, the NDP sugar includes a $^{13}C$ atom. Such labeled compounds are particularly useful in bio-imaging studies, particularly nuclear magnetic resonance (NMR) studies.

Yet another aspect of the invention is directed to a method of providing a glycosylated target molecule. Such a method includes steps of: (a) incubating a nucleotide diphosphate and a glycoside donor in the presence of an isolated mutant glycosyltransferase as described and claimed herein to provide a nucleotide diphosphate (NDP) sugar; and (b) further incubating the NDP sugar with a second glycosyltransferase and a target molecule to provide a glycosylated target molecule.

In certain embodiments, the glycoside donor has the structure:

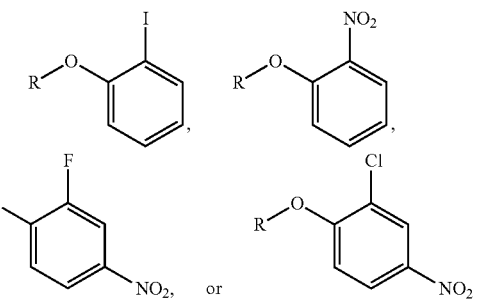

wherein R is β-D-glucopyranose.

In other embodiments, the glycoside donor has the structure:

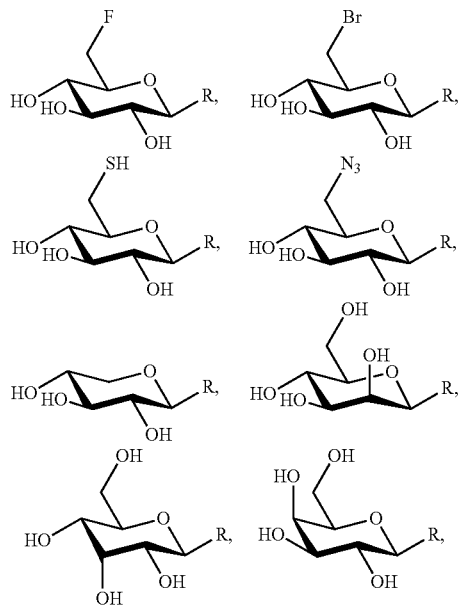

-continued

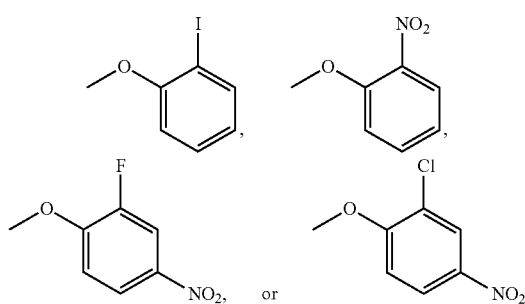

wherein R is:

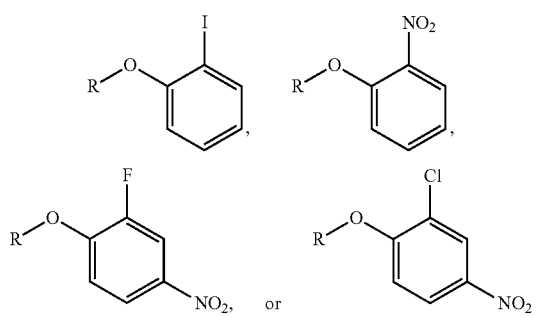

Suitable target molecules for use in the present method include, but are not limited to, natural or synthetic pyran rings, furan rings, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones, flavonoids, isoflavones, coumarins, aminocoumarins, coumarin acids, polyketides, pluramycins, aminoglycosides, oligosaccharides, nucleosides, peptides and proteins.

In alternative embodiments, the method is carried out in vitro, preferably in a single reaction vessel.

In other embodiments, more than one type of target molecule is incubated with the second glycosyltransferase to produce a diverse population of glycosylated target molecules. As well, more than one type of NDP may be incubated with the isolated mutant glycosyltransferase to produce a diverse population of NDP sugars.

The invention further provides an isolated nucleic acid encoding a mutant glycosyltransferase having a polypeptide sequence identical to or substantially identical to OleD glycosyltransferase (SEQ ID NO:1) in which proline at position 67 has been replaced with threonine, serine at position 132 has been replaced with phenylalanine, alanine at position 242 has been replaced with leucine, and glutamine at position 268 has been replaced with valine, wherein the isolated mutant glycosyltransferase exhibits an improved conversion of nucleotide diphosphate (NDP) to NDP sugar as compared to a corresponding non-mutated glycosyltransferase.

In a preferred embodiment, the isolated nucleic acid hybridizes under stringent conditions to the nucleotide sequence set forth in SEQ ID NO:2.

In various related aspects, a recombinant vector comprising the isolated nucleic acid and a host cell comprising same are provided by the invention.

Another aspect of the invention is a fluorescent-based assay for identifying a mutant glycosyltransferase exhibiting an improved conversion of nucleotide diphosphate (NDP) to NDP sugar as compared to a corresponding non-mutated glycosyltransferase. Such a method includes steps of: (a) providing a mutant glycosyltransferase; (b) incubating the mutant glycosyltransferase with an NDP and a fluorescent glycoside donor; and (c) measuring a change in fluorescence intensity of the fluorescent glycoside donor incubated with the mutant glyscosyltransferase, the mutant glycosyltransferase's ability to transfer a sugar from said fluorescent glycoside donor to the NDP to form an NDP sugar indicated by an increase in the fluorescence of the fluorescent glycoside donor incubated with the mutant glycosyltransferase; wherein the mutant glycosyltransferase exhibits an improved conversion of NDP to NDP sugar by displaying an increase in the fluorescent glycoside donor fluorescence as compared to a corresponding non-mutated glycosyltransferase.

In certain embodiments, the glycoside donor has the structure:

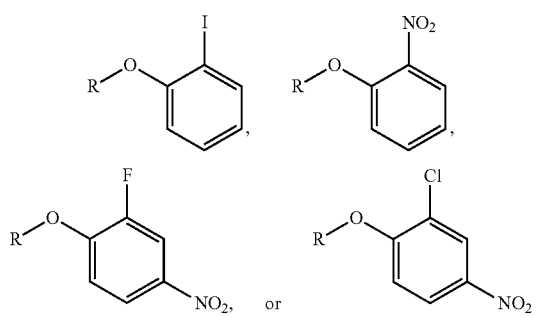

wherein R is β-D-glucopyranose.

In other embodiments, the glycoside donor has the structure:

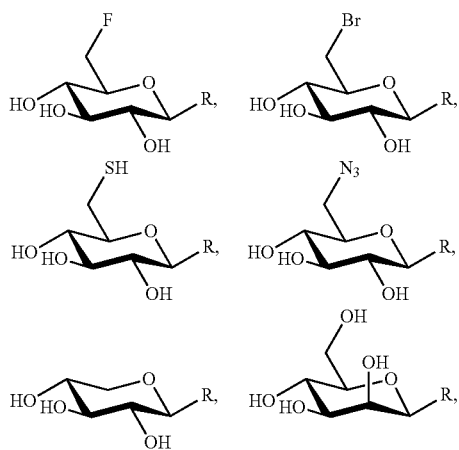

-continued

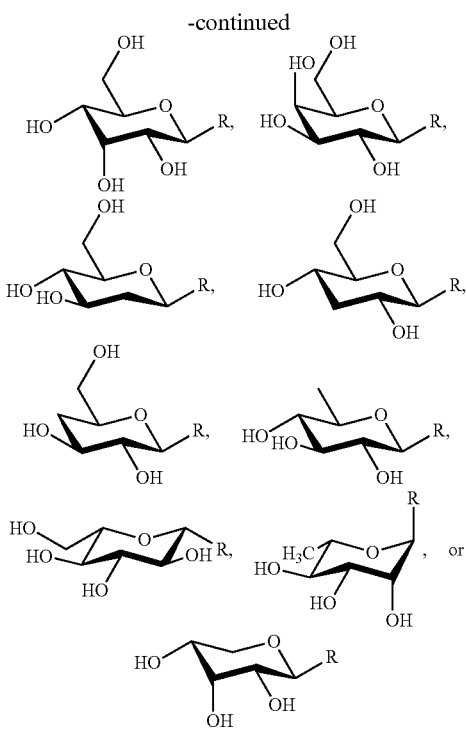

wherein R is:

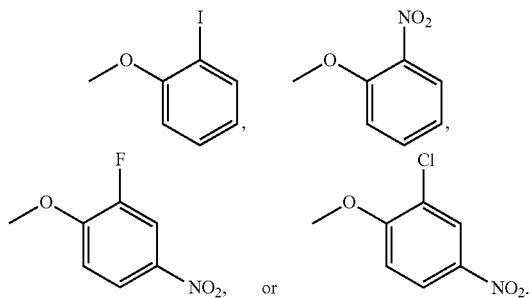

In preferred embodiments, the assay is carried out in parallel on a plurality of mutant glycosyltransferases.

Other objects, features and advantages of the present invention will become apparent after review of the specification, claims and drawings.

DETAILED DESCRIPTION OF THE INVENTION

Figure 1:
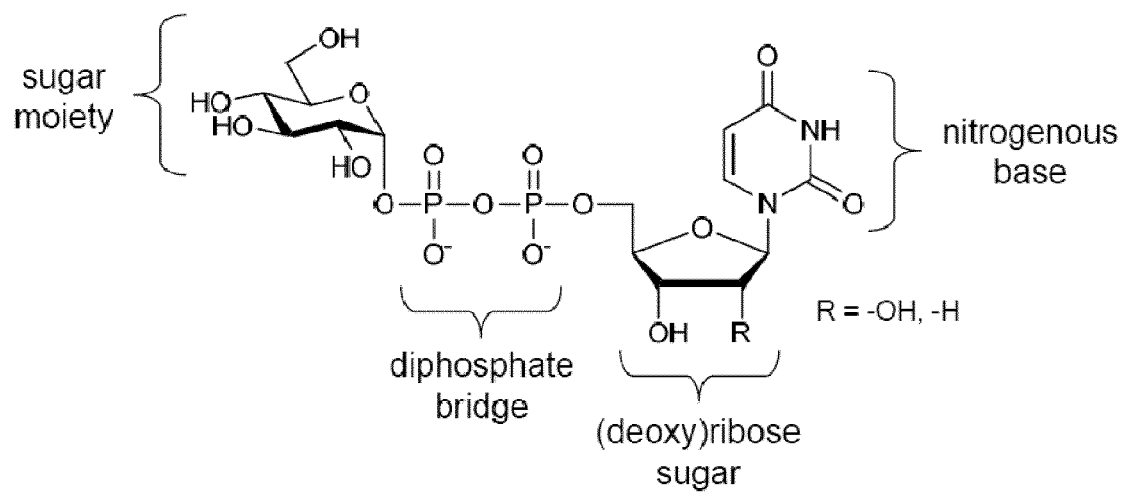
FIG. 1 depicts the general structure of a nucleotide diphosphate (NDP) sugar.
Figure 2:
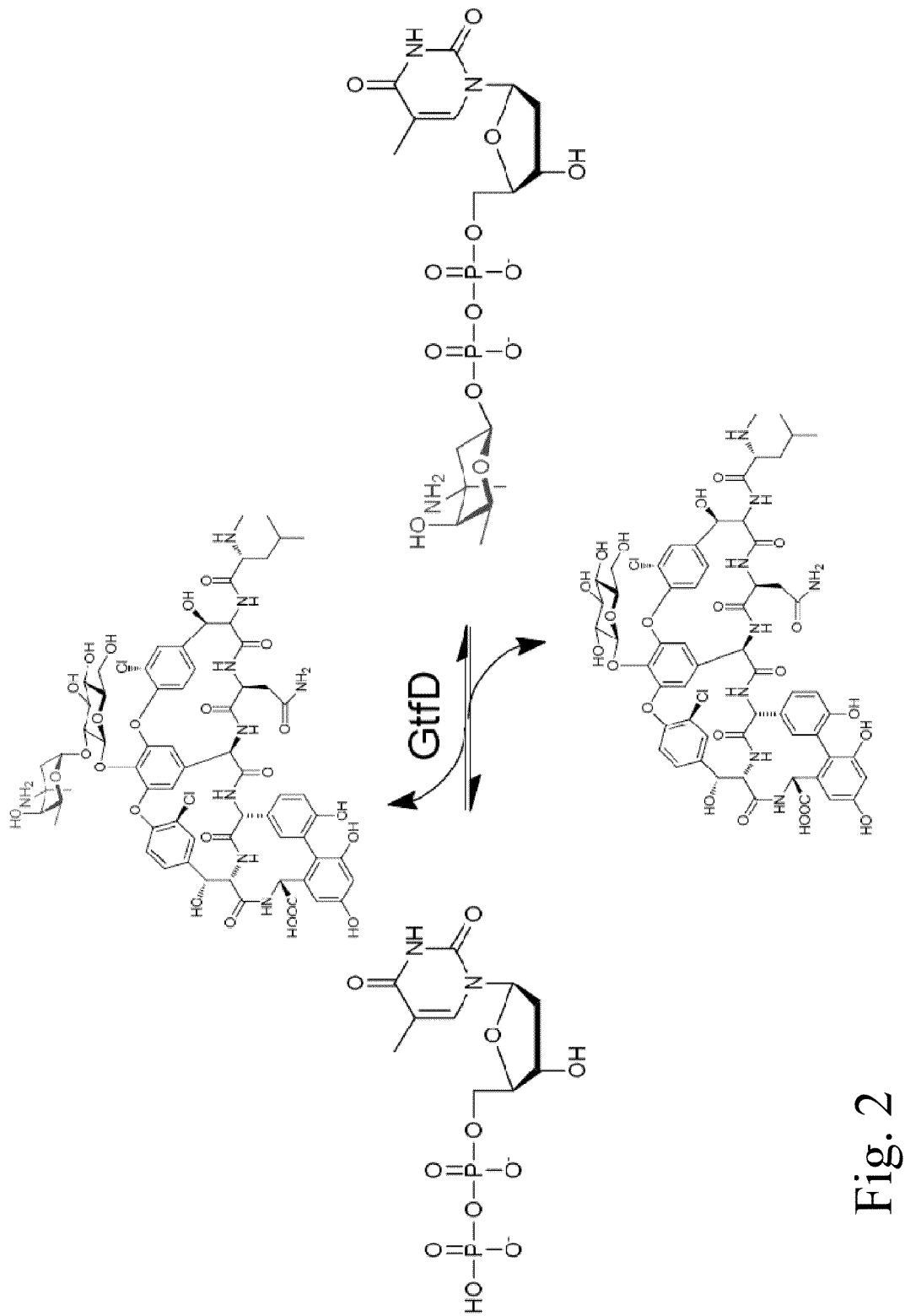
FIG. 2 shows the reaction catalyzed by GtfD which utilizes an NDP sugar as a donor substrate.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

A "host cell" is a cell which has been transformed or transfected, or is capable of transformation or transfection by an exogenous polynucleotide sequence. A host cell that has been transformed or transfected may be more specifically referred to as a "recombinant host cell". Preferred host cells for use in methods of the invention include bacterial cells, particularly *E. coli*.

The polypeptide sequence for the wild type OleD protein is provided below as SEQ ID NO: 1:

```
                                                  (SEQ ID NO: 1)
MTTQTTPAHIAMFSIAAHGHVNPSLEVIRELVARGHRVTYAIPPVFAD

KVAATGARPVLYHSTLPGPDADPEAWGSTLLDNVEPFLNDAIQALPQL

ADAYADDIPDLVLHDITSYPARVLARRWGVPAVSLSPNLVAWKGYEEE

VAEPMWREPRQTERGRAYYARFEAWLKENGITEHPDTFASHPPRSLVL

IPKALQPHADRVDEDVYTFVGACQGDRAEEGGWQRPAGAEKVVLVSLG

SAFTKQPAFYRECVRAFGNLPGWHLVLQIGRKVTPAELGELPDNVEVH

DWVPQLAILRQADLFVTHAGAGGSQEGLATATPMIAVPQAVDQFGNAD

MLQGLGVARKLATEEATADLLRETALALVDDPEVARRLRRIQAEMAQE

GGTRRAADLIEAELPARHERQEPVGDRPNGG
```

An exemplary nucleotide sequence which encodes the wild type OleD protein is set forth below as SEQ ID NO: 2:

A polypeptide "substantially identical" to a comparative polypeptide varies from the comparative polypeptide, but has at least 80%, preferably at least 85%, more preferably at least 90%, and yet more preferably at least 95% sequence identity at the amino acid level over the complete amino acid sequence, and, in addition, it possesses the ability to improve conversion of NDP to NDP sugars.

The term "substantial sequence homology" refers to DNA or RNA sequences that have de minimus sequence variations from, and retain substantially the same biological functions as the corresponding sequences to which comparison is made. In the present invention, it is intended that sequences having substantial sequence homology to the nucleic acid of SEQ ID NO:2 are identified by: (1) their encoded gene product possessing the ability to improve conversion of NDP to NDP sugar; and (2) their ability to hybridize to the sequence of SEQ ID NO: 2, respectively, under stringent conditions.

As used herein, "hybridizes under stringent conditions" is intended to describe conditions for hybridization and washing under which nucleotide sequences that are significantly identical or homologous to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions

```
                                                             (SEQ ID NO: 2)
atgaccaccc agaccactcc cgcccacatc gccatgttct ccatcgccgc ccacggccat gtgaacccca gcctggaggt gatccgtgaa ctcgtcgccc gcggccaccg ggtcacgtac gccattccgc ccgtcttcgc cgacaaggtg gccgccaccg gcgcccggcc cgtcctctac cactccaccc tgcccggccc cgacgccgac ccggaggcat ggggaagcac cctgctggac aacgtcgaac cgttcctgaa cgacgcgatc caggcgctcc cgcagctcgc cgatgcctac gccgacgaca tccccgatct cgtcctgcac gacatcacct cctacccggc ccgcgtcctg gcccgccgct ggggcgtccc ggcggtctcc ctctccccga acctcgtcgc ctggaagggt tacgaggagg aggtcgccga gccgatgtgg cgcgaacccc ggcagaccga gcgcggacgg gcctactacg cccggttcga ggcatggctg aaggagaacg ggatcaccga gcacccggac acgttcgcca gtcatccgcc gcgctccctg gtgctcatcc cgaaggcgct ccagccgcac gccgaccggg tggacgaaga cgtgtacacc ttcgtcggcg cctgccaggg agaccgcgcc gaggaaggcg gctggcagcg gcccgccggc gcggagaagg tcgtcctggt gtcgctcggc tcggcgttca ccaagcagcc cgccttctac cgggagtgcg tgcgcgcctt cgggaacctg cccggctggc acctcgtcct ccagatcggc cggaaggtga ccccgccga actggggag ctgccggaca acgtggaggt gcacgactgg gtgccgcagc tcgcgatcct gcgccaggcc gatctgttcg tcacccacgc gggcgccggc ggcagccagg aggggctggc caccgcgacg cccatgatcg ccgtaccgca ggccgtcgac cagttcggca acgccgacat gctccaaggg ctcggcgtcg cccggaagct ggcgaccgag gaggccaccg ccgacctgct ccgcgagacc gccctcgctc tggtggacga cccggaggtc gcgcgccggc tccggcggat ccaggcggag atggcccagg agggcggcac ccggcgggcg gccgacctca tcgaggccga actgccccgcg cgccacgagc ggcaggagcc ggtgggcgac cgacccaacg gtgggtga
``` includes hybridization in 4× sodium chlorine/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 4×SSC plus 50% formamide at about 42-50° C.) followed by one or more washes in 0.3×SSC, at about 65-70° C. A preferred, non-limiting example of highly stringent hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM $NaH_2PO_4$, and 1.25 mM EDTA, pH 7.4) can be substituted for SSC (1×SSPE is 0.15 M NaC and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids between 18 and 49 base pairs in length, $T_m$ (° C.)=81.5+16.6($log_{10}$[Na+])+0.41(% G+C)−(600/N), where N is the number of bases in the hybrid, and [Na+] is the concentration of sodium ions in the hybridization buffer ([Na+] for 1×SSC=0.165 M). It will also be recognized by the skilled practitioner that additional reagents may be added to the hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS) chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washed at 0.02M $NaH_2PO_4$, 1% SDS at 65° C., see e.g., Church and Gilbert (1984) Proc. Natl. Acad. Sci. USA 81: 1991-1995, (or alternatively 0.2×SSC, 1% SDS).

"Polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

The term "isolated nucleic acid" used in the specification and claims means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene. Specifically excluded from this definition are nucleic acids present in mixtures of clones, e.g., as those occurring in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine, as described in a preceding definition.

The term "operably linked" means that the linkage (e.g., DNA segment) between the DNA segments so linked is such that the described effect of one of the linked segments on the other is capable of occurring. "Linked" shall refer to physically adjoined segments and, more broadly, to segments which are spatially contained relative to each other such that the described effect is capable of occurring (e.g., DNA segments may be present on two separate plasmids but contained within a cell such that the described effect is nonetheless achieved). Effecting operable linkages for the various purposes stated herein is well within the skill of those of ordinary skill in the art, particularly with the teaching of the instant specification.

As used herein the term "gene product" shall refer to the biochemical material, either RNA or protein, resulting from expression of a gene.

The term "heterologous" is used for any combination of DNA sequences that is not normally found intimately associated in nature (e.g., a green fluorescent protein (GFP) reporter gene operably linked to a SV40 promoter). A "heterologous gene" shall refer to a gene not naturally present in a host cell (e.g., a luciferase gene present in a retinoblastoma cell line).

As used herein, the term "homolog" refers to a gene related to a second gene by descent from a common ancestral DNA sequence. The term, homolog, may apply to the relationship between genes separated by the event of speciation (i.e., orthologs) or to the relationship between genes separated by the event of genetic duplication (i.e., paralogs). "Orthologs" are genes in different species that evolved from a common ancestral gene by speciation. Normally, orthologs retain the same function in the course of evolution. Identification of orthologs is important for reliable prediction of gene function in newly sequenced genomes. "Paralogs" are genes related by duplication within a genome. Orthologs retain the same function in the course of evolution, whereas paralogs evolve new functions, even if these are related to the original one.

The nucleotides that occur in the various nucleotide sequences appearing herein have their usual single-letter designations (A, G, T, C or U) used routinely in the art. In the present specification and claims, references to Greek letters may either be written out as alpha, beta, etc. or the corresponding Greek letter symbols (e.g., α, β, etc.) may sometimes be used.

The following abbreviations are used herein: GT, glycosyltransferase; NTP, nucleotide-5'-triphosphate; ATP, adenosine-5'-triphosphate; CTP, cytidine-5'-triphosphate; GTP, guanosine-5'-triphosphate; UTP, uridine-5'-triphosphate; dATP, 2'-deoxyadenosine-5'-triphosphate; dCTP, 2'-deoxycytidine-5'-triphosphate; dGTP, 2'-deoxyguanosine-5'-triphosphate; dTTP, 2' deoxythymidine-5'-triphosphate; NDP-sugar, nucleotide diphosphosugar; IPTG, isopropyl-β-D-thiogalactopyranoside; and WT, wild-type.

Glycosyltransferases (GTs), an essential class of ubiquitous enzymes, are generally perceived as unidirectional catalysts. However, the present invention teaches that GTs catalyze readily reversible reactions, allowing sugars and aglycons to be exchanged. Thus, the reversibility of GT-catalyzed reactions is useful for the rapid synthesis of exotic nucleotide sugars, establishing in vitro GT activity in complex systems, and enhancing natural product diversity.

Figure 4:
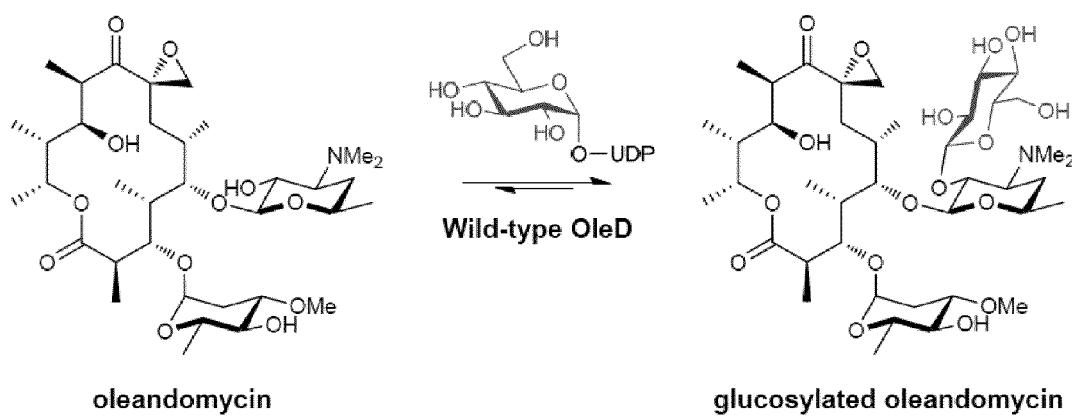
FIG. 4 depicts the reaction catalyzed by wild type OleD. OleD was mutated to accept three different nitrogenous bases, approximately 20 sugars, and approximately 90 aglycons.

The present invention is based on the inventors' success in broadening the promiscuity of a natural product GT—the oleandomycin GT (OleD) from *Streptomyces antibioticus*. The native macrolide GT reaction catalyzed by OleD was previously characterized and is shown in FIG. 4.

Using a high throughput screen based upon a fluorescent glycoside donor, the inventors have identified from a small library of random OleD mutants a number of OleD variants with improved activities toward a range of alternative donor substrates. This work provides a template for engineering other natural product GTs, and highlights variant GTs for the glycorandomization of a range of therapeutically important acceptors including aminocoumarins, flavonoids and macrolides.

Figure 5:
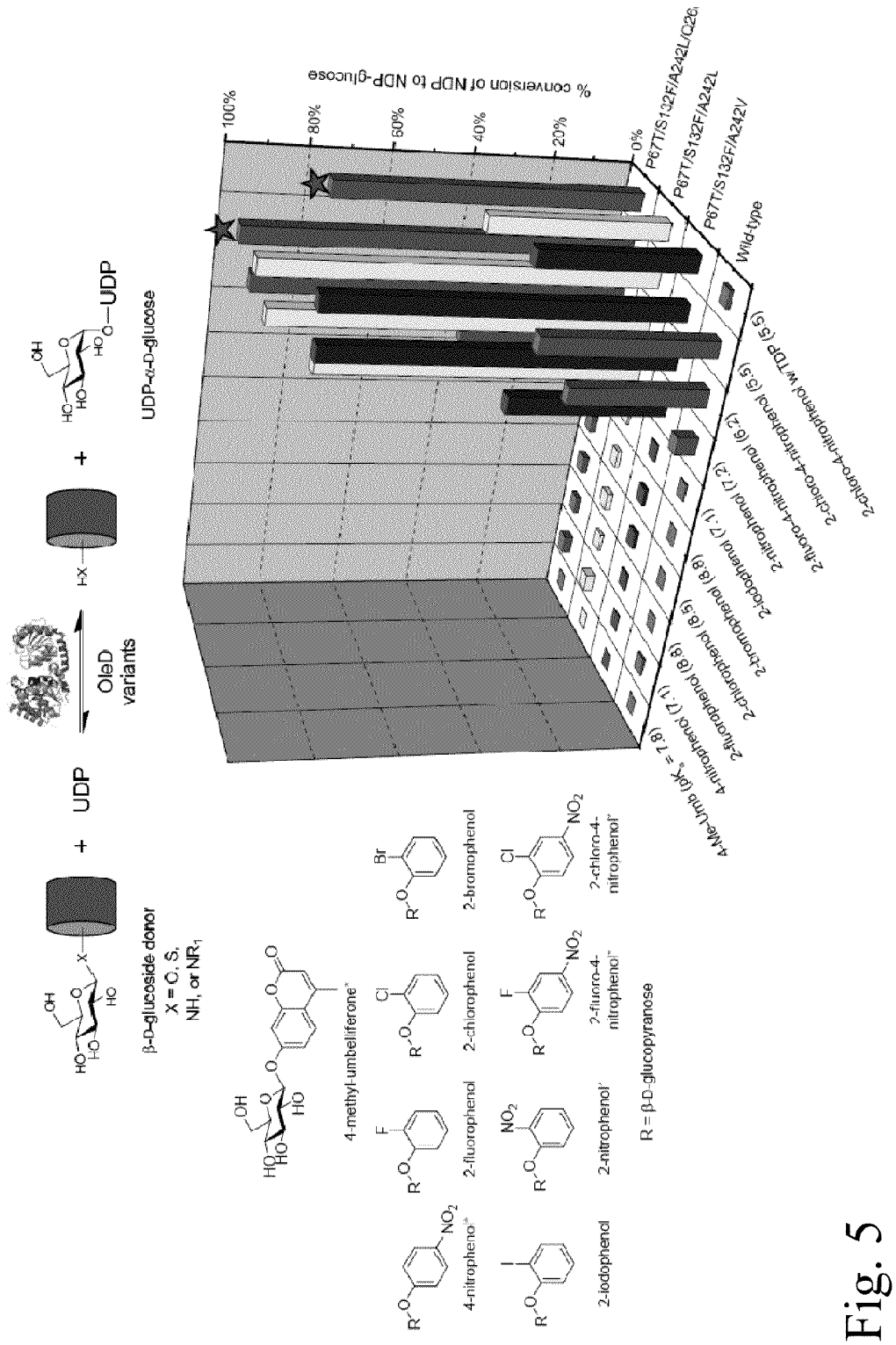
FIG. 5 illustrates the inventors' strategy and results for β-D-glucoside screening of OleD variants.
Figure 6:
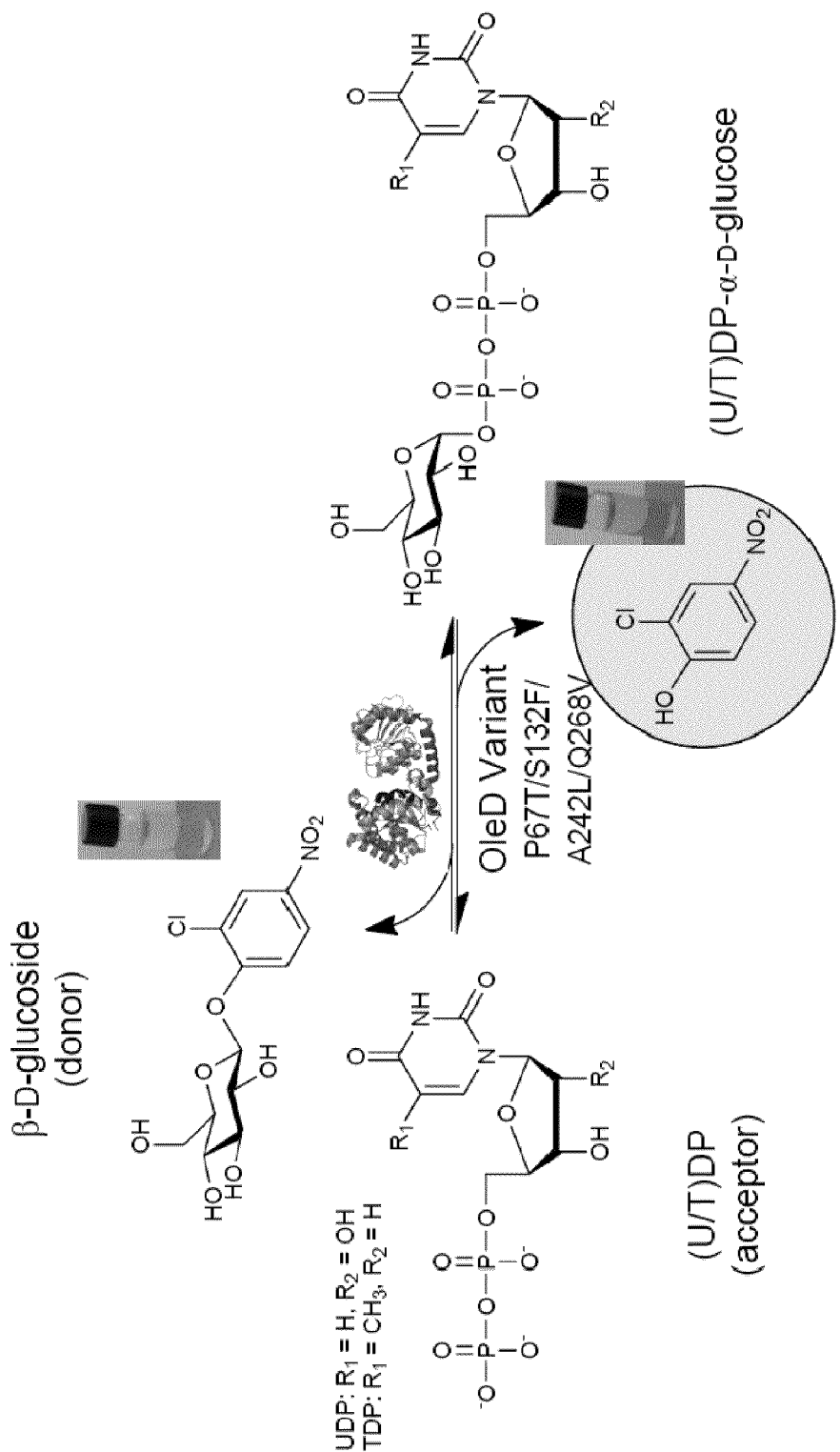
FIG. 6 shows the inventors' identification of OleD variant P67T/S132F/A242L/Q268V and optimization of reverse reaction conditions.
Figure 7:
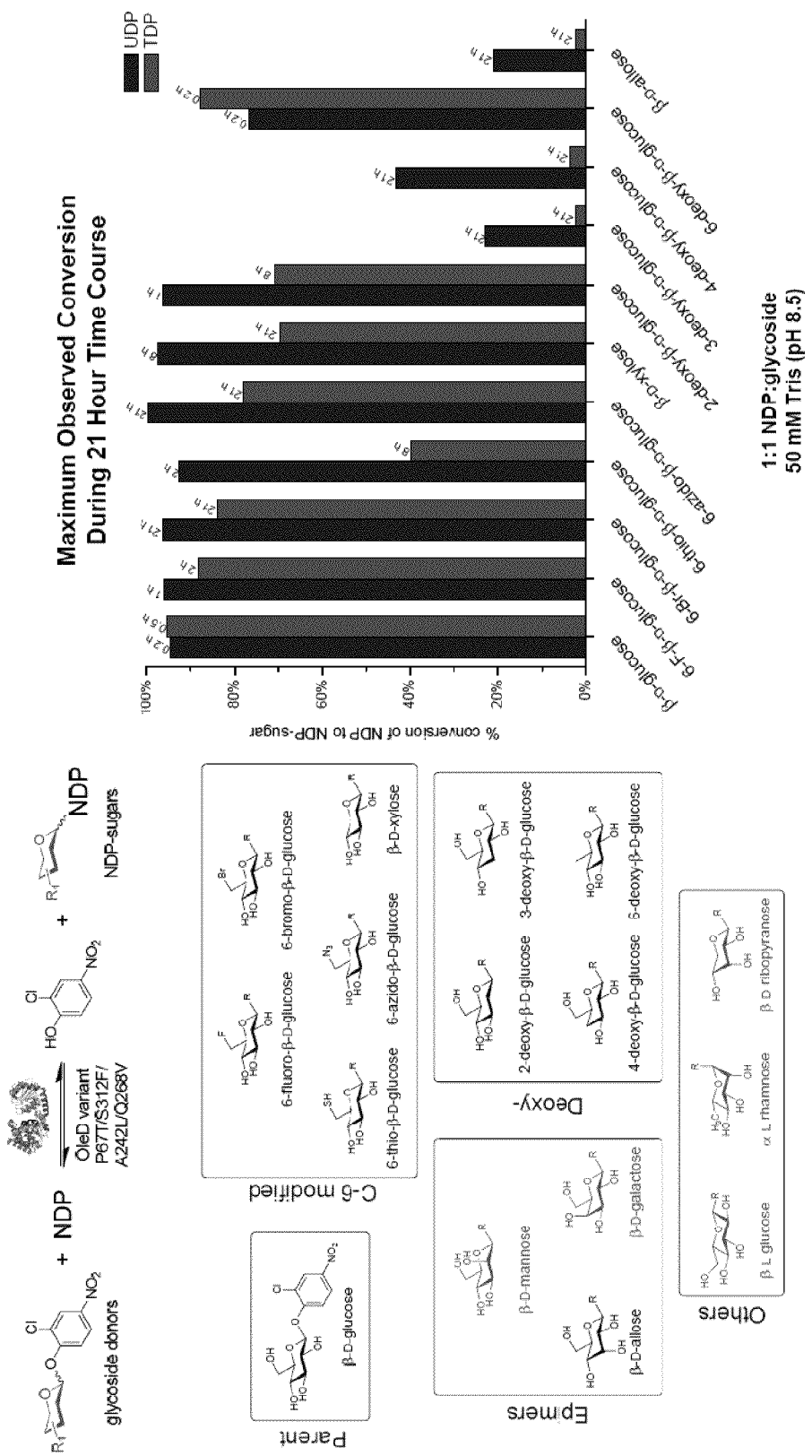
FIG. 7 depicts the inventors' strategy and results for glycoside library evaluation.
Figure 8:
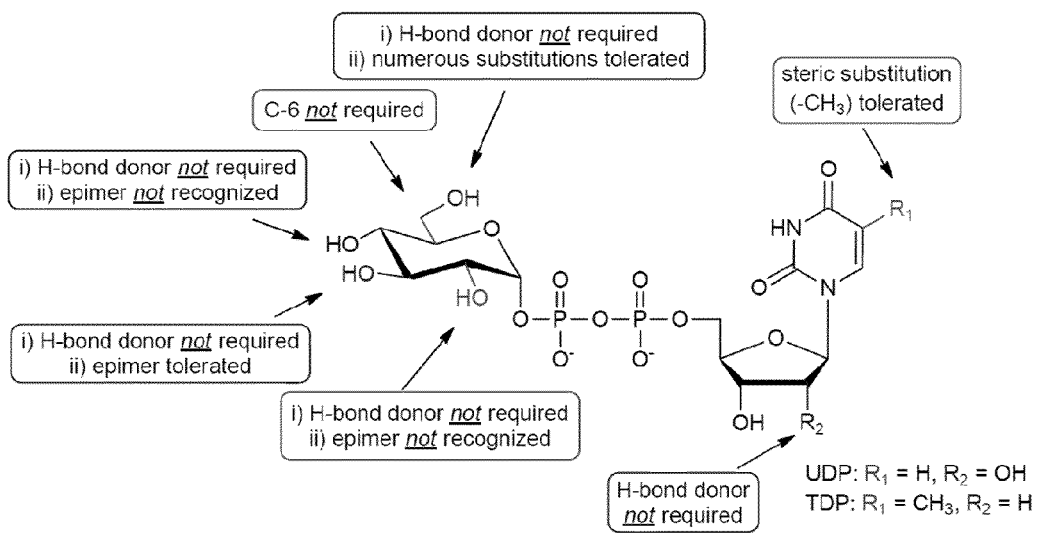
FIG. 8 depicts the inventors' conclusions for structure activity relationship (SAR) evaluation of NDP sugar substrates related to OleD variant substrate usage.

Another aspect of the invention is a versatile method for optimizing glycosyltransferases such as OleD toward non-natural donors through a comprehensive program of 'hot spot' saturation mutagenesis of functional positions. The method comprises a general enzyme optimization strategy (hot spot saturation mutagenesis) applicable to reactions limited by amenable high throughput screens using the macrolide glycosyltransferase OleD as a non-limiting model. Specifically, a high throughput screen based on synthetic glycoside donors is used to identify key amino acid 'hot spots' that contribute to GT conversion of NDP to NDP sugar. FIG. 5 illustrates the inventors' experimental strategy and results for three OleD variants assayed in combination with various synthetic glycoside donors designed to transfer a β-D-glucopyranose moiety. FIG. 6 depicts further optimization of the reaction conditions for the OleD variant P67T/S132F/A242L/Q268V. FIG. 7 illustrates conversion of NDP to NDP sugar for the same respective quadruple mutant utilizing a variety of 2-chloro-4-nitrophenol glycosyl donors, including donors for transferring exemplary sugar moieties such as β-D-glucose, C-6 modified versions of β-D-glucose, epimers of β-D-glucose, deoxy-variants of β-D-glucose, and other related sugars. Using this approach, the inventors generated 22 NDP sugars in a matter of hours. FIG. 8 depicts the inventors' conclusions regarding the structure activity relationship (SAR) between the present OleD variants and NDP sugar structures.

Accordingly, the invention provides in a first aspect an isolated mutant glycosyltransferase comprising: (a) the amino acid sequence of OleD glycosyltransferase set forth in SEQ ID NO:1, wherein proline at position 67 has been replaced with threonine, serine at position 132 has been replaced with phenylalanine, alanine at position 242 has been replaced with leucine, and glutamine at position 268 has been replaced with valine; or (b) an amino acid sequence substantially identical to OleD glycosyltransferase (SEQ ID NO:1) in which proline at position 67 has been replaced with threonine, serine at position 132 has been replaced with phenylalanine, alanine at position 242 has been replaced with leucine, and glutamine at position 268 has been replaced with valine; wherein the isolated mutant exhibits an improved conversion of nucleotide diphosphate (NDP) to NDP sugar as compared to a corresponding non-mutated glycosyltransferase. In preferred embodiments, the isolated mutant glycosyltransferase is encoded by a nucleotide that hybridizes under stringent conditions to the nucleotide sequence set forth in SEQ ID NO:2.

In a second aspect, the invention provides a method of providing an isolated mutant glycosyltransferase with improved conversion of nucleotide diphosphate (NDP) to NDP sugar as compared to a corresponding non-mutated glycosyltransferase. Such a method includes steps of: (a) mutating an isolated nucleic acid sequence encoding an amino acid sequence identical to or substantially identical to OleD glycosyltransferase (SEQ ID NO:1) in which proline at position 67 has been replaced with threonine, serine at position 132 has been replaced with phenylalanine, alanine at position 242 has been replaced with leucine, and glutamine at position 268 has been replaced with valine; (b) expressing said isolated nucleic acid in a host cell; and (c) isolating from the host cell a mutant glycosyltransferase that is characterized by improved conversion of nucleotide diphosphate (NDP) to NDP sugar as compared to a corresponding non-mutated glycosyltransferase.

Figure 9:
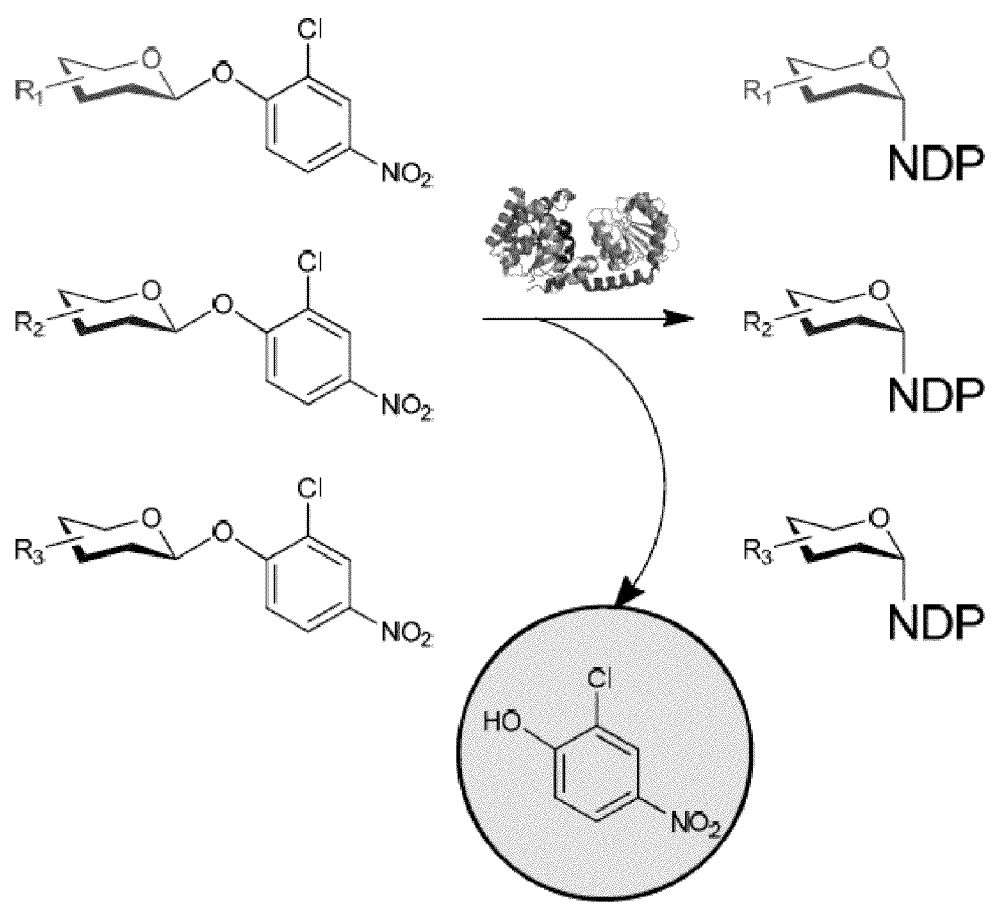
FIG. 9 illustrates a general scheme for production of milligram scale NDP-sugar libraries for biochemicaliInvestigations and drug discovery.

In another aspect, the invention encompasses a method of providing a nucleotide diphosphate (NDP) sugar. Such a method includes steps of incubating a nucleotide diphosphate and a glycoside donor in the presence of an isolated mutant glycosyltransferase described and claimed herein to provide an NDP sugar. FIG. 9 illustrates a general schematic for such a method using one of the synthetic glycoside donors explicitly described below.

In certain methods, the glycoside donor has the structure:

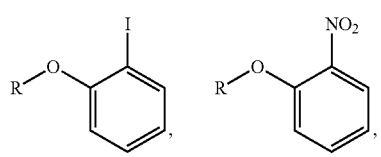

-continued

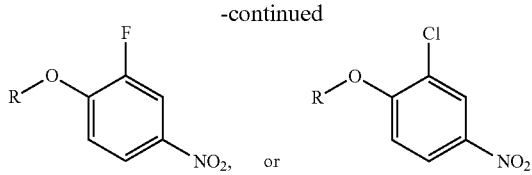

wherein R is β-D-glucopyranose.
In other embodiments, the glycoside donor has the structure:

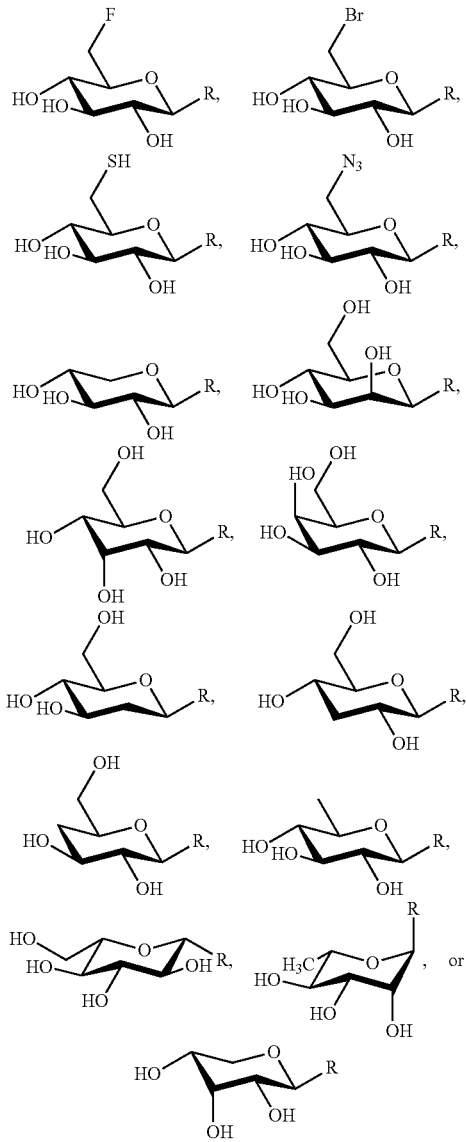

wherein R is:

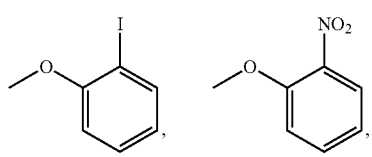

-continued

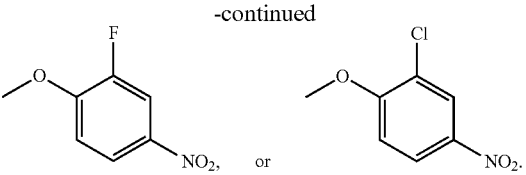

Figure 10:
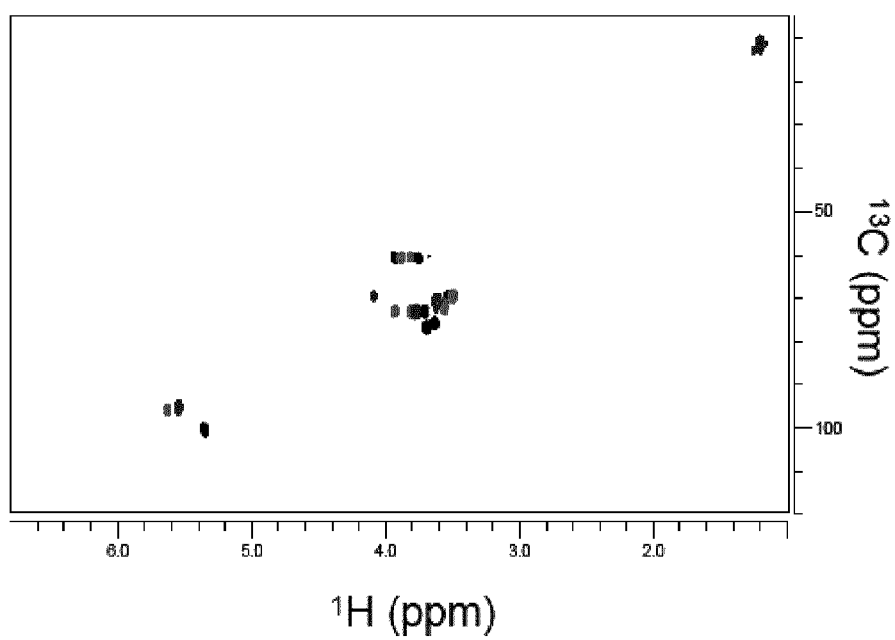
FIG. 10 depicts production of $^{13}C$ Labeled NDP-sugars for bioimaging studies.
Figure 10:
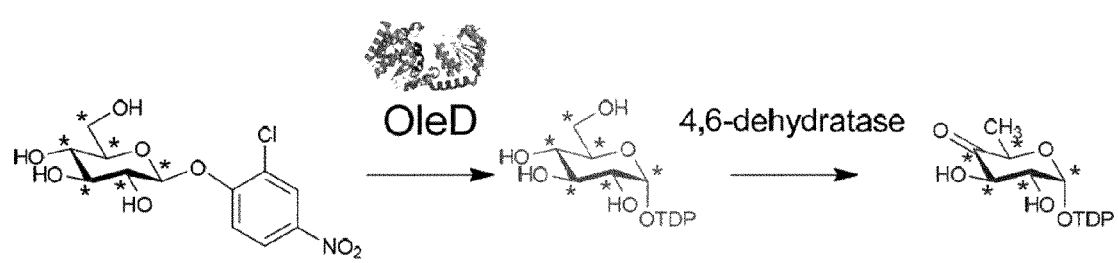

The NDP is preferably uridine or thymidine diphosphate. In alternative embodiments, the NDP sugar includes a $^{13}C$ atom. Such labeled compounds are particularly useful for bioimaging studies, specifically nuclear magnetic resonance (NMR) imaging. FIG. 10 depicts an NMR study utilizing a $^{13}C$-labeled NDP sugar.

Figure 12:
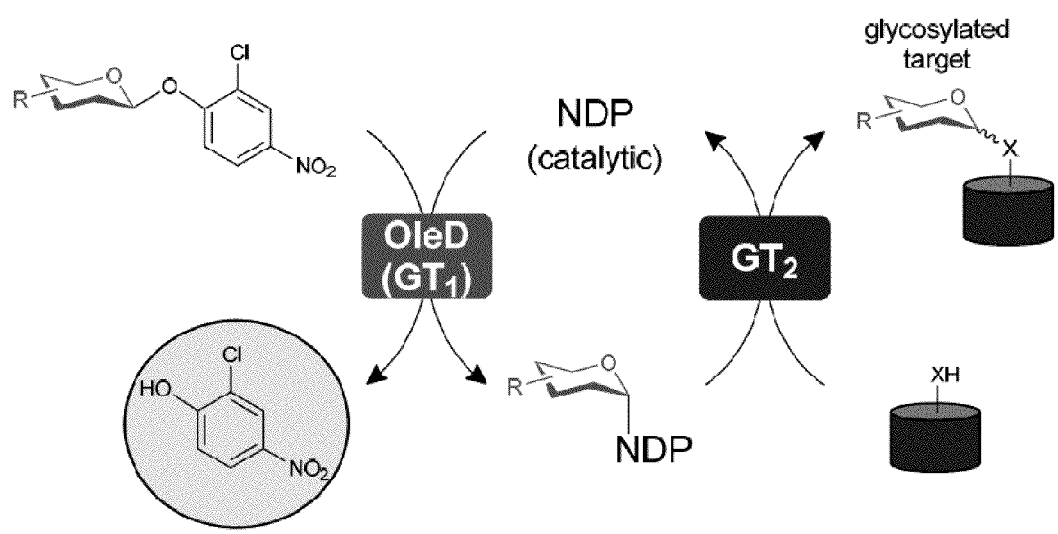
FIG. 12 depicts the coupling of GT reactions to initially provide an NDP sugar which serves as the glycoside donor in a second GT reaction to provide a glycosylated target.

Yet another aspect of the invention is directed to a method of providing a glycosylated target molecule. Such a method includes steps of: (a) incubating a nucleotide diphosphate and a glycoside donor in the presence of an isolated mutant glycosyltransferase as described and claimed herein to provide a nucleotide diphosphate (NDP) sugar; and (b) further incubating the NDP sugar with a second glycosyltransferase and a target molecule to provide a glycosylated target molecule. FIG. 12 depicts a general scheme in which an OleD variant according to the invention is coupled with a second different GT to provide a glycosylated target molecule.

In certain embodiments, the glycoside donor has the structure:

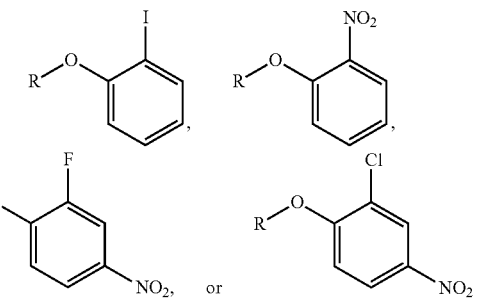

wherein R is β-D-glucopyranose.
In other embodiments, the glycoside donor has the structure:

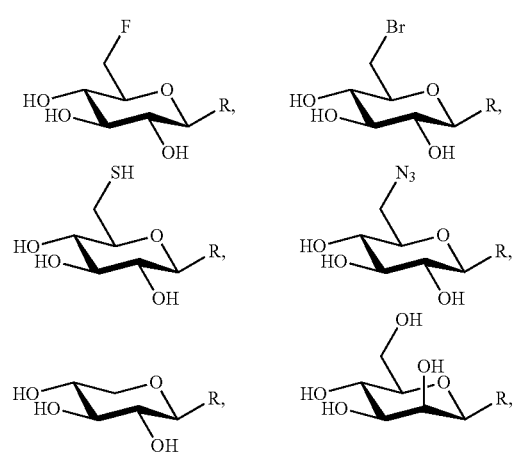

-continued

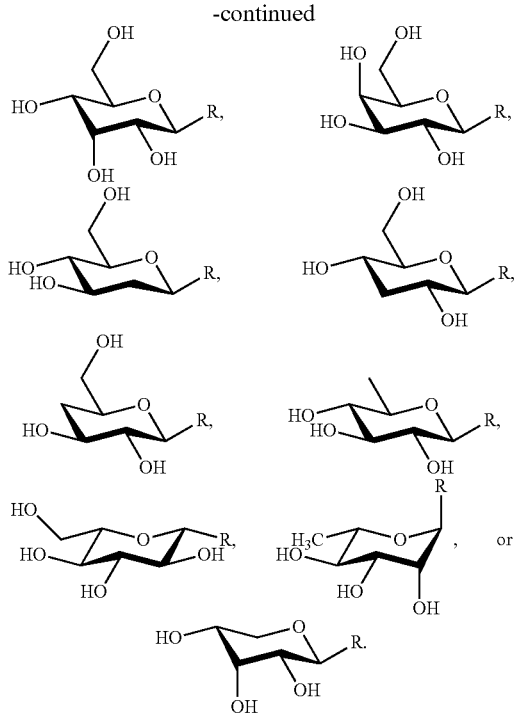

wherein R is:

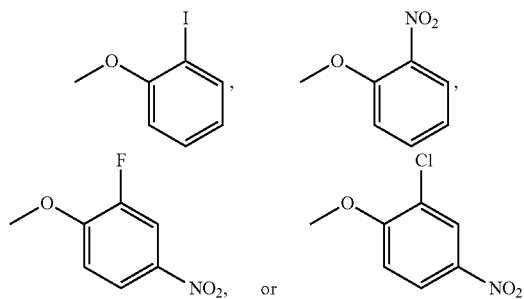

Suitable target molecules for use in the present method include, but are not limited to, natural or synthetic pyran rings, furan rings, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones, flavonoids, isoflavones, coumarins, aminocoumarins, coumarin acids, polyketides, pluramycins, aminoglycosides, oligosaccharides, nucleosides, peptides and proteins.

In alternative embodiments, the method is carried out in vitro, preferably in a single reaction vessel.

In other embodiments, more than one type of target molecule is incubated with the second glycosyltransferase to produce a diverse population of glycosylated target molecules. As well, more than one type of NDP may be incubated with the isolated mutant glycosyltransferase to produce a diverse population of NDP sugars.

The invention further provides an isolated nucleic acid encoding a mutant glycosyltransferase having a polypeptide sequence identical to or substantially identical to OleD glycosyltransferase (SEQ ID NO:1) in which proline at position 67 has been replaced with threonine, serine at position 132 has been replaced with phenylalanine, alanine at position 242 has been replaced with leucine, and glutamine at position 268 has been replaced with valine, wherein the isolated mutant glycosyltransferase exhibits an improved conversion of nucleotide diphosphate (NDP) to NDP sugar as compared to a corresponding non-mutated glycosyltransferase.

In a preferred embodiment, the isolated nucleic acid hybridizes under stringent conditions to the nucleotide sequence set forth in SEQ ID NO:2.

In various related aspects, a recombinant vector comprising the isolated nucleic acid and a host cell comprising same are provided by the invention.

Another aspect of the invention is a fluorescent-based assay for identifying a mutant glycosyltransferase exhibiting an improved conversion of nucleotide diphosphate (NDP) to NDP sugar as compared to a corresponding non-mutated glycosyltransferase. Such a method includes steps of: (a) providing a mutant glycosyltransferase; (b) incubating the mutant glycosyltransferase with an NDP and a fluorescent glycoside donor; and (c) measuring a change in fluorescence intensity of the fluorescent glycoside donor incubated with the mutant glyscosyltransferase, the mutant glycosyltransferase's ability to transfer a sugar from said fluorescent glycoside donor to the NDP to form an NDP sugar indicated by an increase in the fluorescence of the fluorescent glycoside donor incubated with the mutant glycosyltransferase; wherein the mutant glycosyltransferase exhibits an improved conversion of NDP to NDP sugar by displaying an increase in the fluorescent glycoside donor fluorescence as compared to a corresponding non-mutated glycosyltransferase.

In certain embodiments, the glycoside donor has the structure:

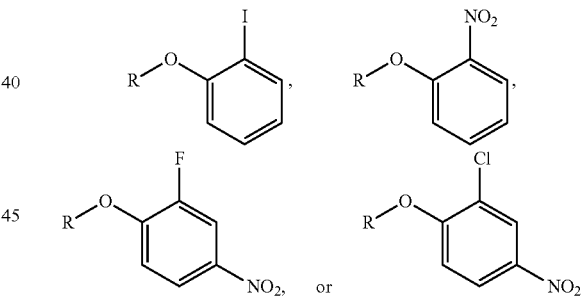

wherein R is β-D-glucopyranose.

In other embodiments, the glycoside donor has the structure:

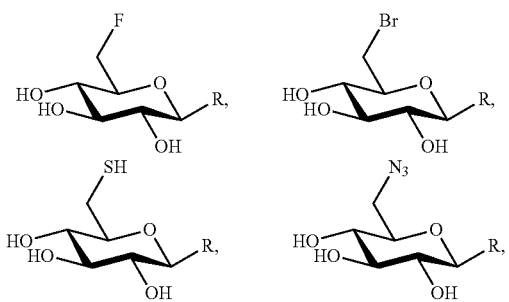

-continued

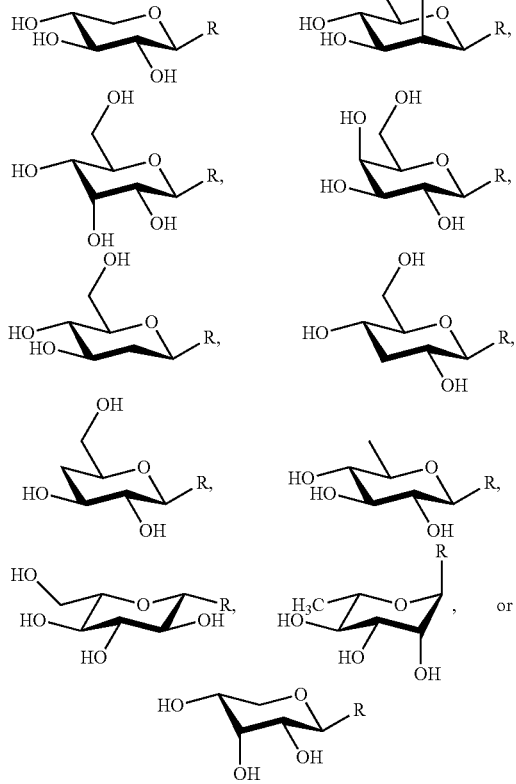

wherein R is:

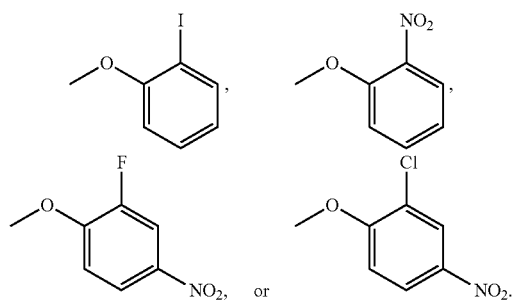

Figure 11:
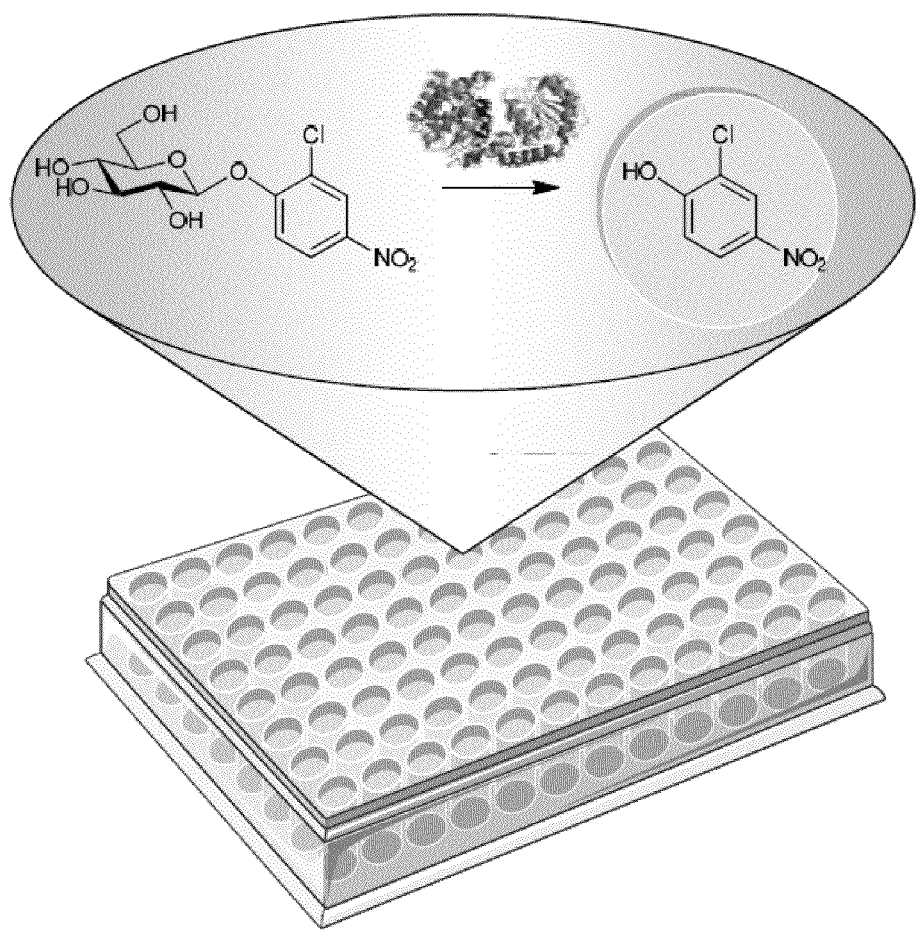
FIG. 11 depicts a general strategy for protein engineering and evolution based on the OleD variants.

In preferred embodiments, the assay is carried out in parallel on a plurality of mutant glycosyltransferases. FIG. 11 illustrates an assay according to the invention carried out in a multiwall format.

Figure 13:
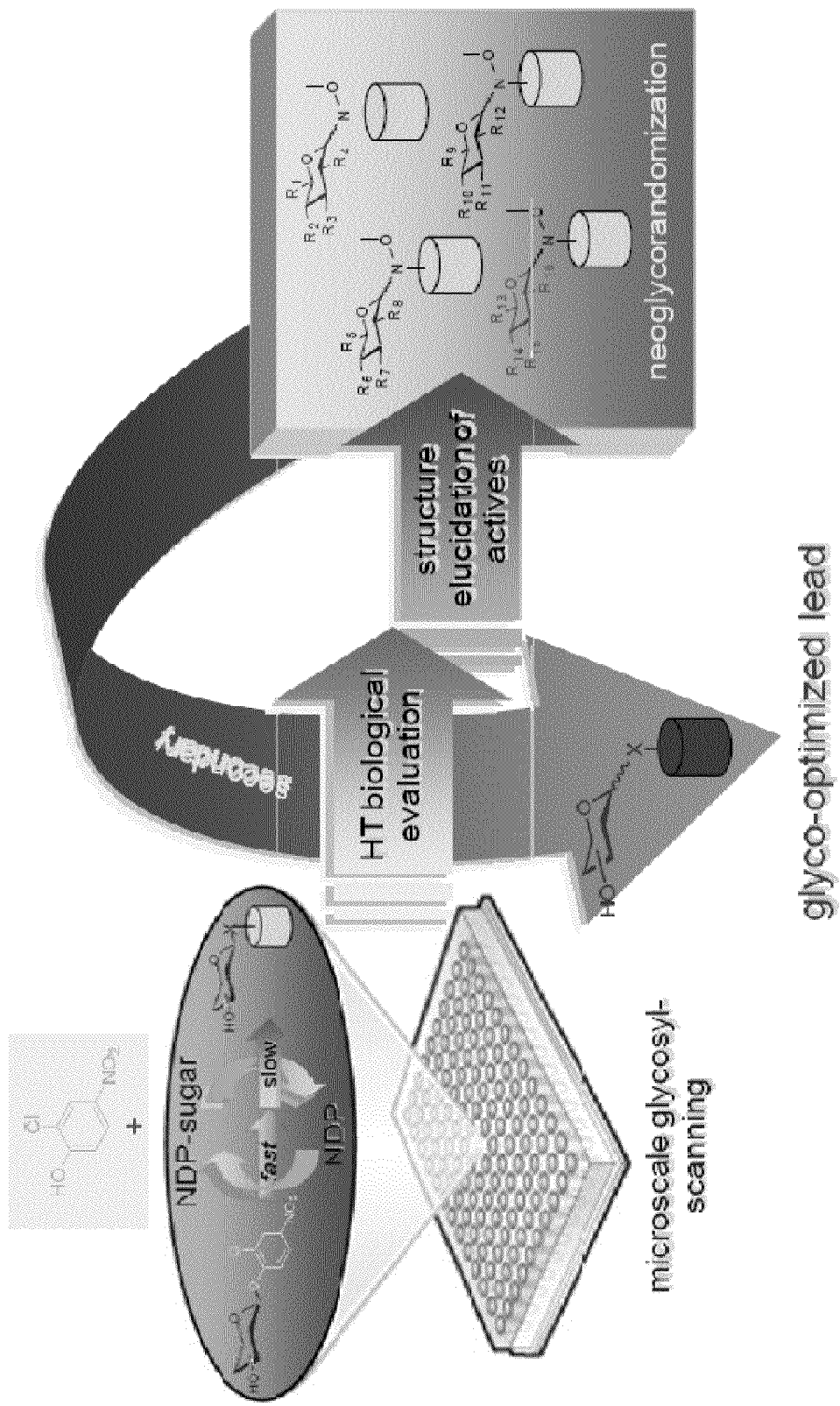
FIG. 13 illustrates an approach to microscale glycosyl scanning according to the invention.

As can be appreciated, the invention provides a systematic strategy for the development of integrated high throughput pipelines to rapidly synthesize and evaluate sugar-drug conjugates—referred to as microscale glycosyl-scanning (shown generally in FIG. 13). The core innovation of this study is an unparalleled one-step glycosyltransferase (GT)-catalyzed transglycosylation reaction from simple activated (2-chloro-4-nitrophenol) glycosyl donors that ultimately drives subsequent target scaffold glycosylation while providing a convenient colorimetric readout amenable to high throughput screening. The development of this strategy utilized a novel evolved GT, a highly proficient GT for TTP/TDP, and one that lacks unwanted 'hydrolytic' activity) and the screening of a wide array of potential donor glycosides (focusing upon those capable of presenting a fluorescent or colorimetric signal upon sugar nucleotide formation). Based upon this initial analysis, 2-chloro-4-nitrophenol glycosyl donors were found to heavily favor sugar nucleotide formation and the utility of this GT-catalyzed reaction subsequently was demonstrated with 11 diverse donors using both UDP and TDP. This study clear sets the stage for microscale scanning (toward either diverse drug and/or sugar scaffolds).

The following experimental data are provided to illustrate the invention. It is to be understood that a person skilled in the art who is familiar with the methods may use other yeast strains, recombinant vectors, and methodology which can be equally used for the purpose of the present invention. These alterations are included in the scope of the invention.

EXAMPLES

Materials

Figure 3:
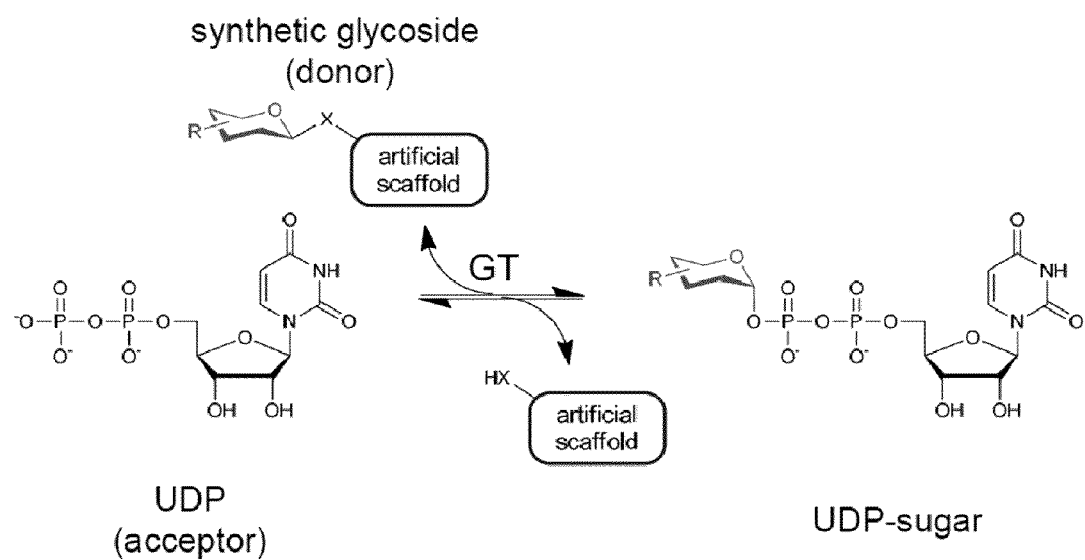
FIG. 3 illustrates glycosyltransferase (GT) reversibility and the utilization of a synthetic glycoside donor.

Bacterial strain *E. coli* BL21(DE3)pLysS was from Stratagene. NovaBlue was from Novagen. Plasmid pET28/OleD was a generous gift from Prof Hung-Wen Liu (University of Texas-Austin, Austin, USA) and pET28a was from Novagen. All other chemicals were reagent-grade purchased from Fluka, New England Biolabs, or Sigma, unless otherwise stated. Primers were ordered from Integrated DNA Technologies (Coralville, Iowa). Oleandomycin was purchased from MP Biomedicals Inc. (Ohio, USA). Phenolic substrates (Table 1: 27, 28, 30-32) were from Indofine Chemical Company Inc. (Hillsborough, N.J., USA). Novobiocic acid (Table 1: 29) was prepared as previously described from Novobiocin. Albermann C, et al. (2003) *Org Lett* 5: 933-6. Product standard 4-Me-umb-7-O-beta-D-glucoside (FIG. 1: 4-glc) was from Sigma, daidzein-7-O-beta-D-glucoside (Table 1: 31-glc), and genistein-7-O-beta-D-glucoside (Table 1: 32-glc) standards were from Fluka. Analytical HPLC was performed on a Rainin Dynamax SD-2/410 system connected to a Rainin Dynamax UV-DII absorbance detector. Mass spectra were obtained using electrospray ionization on an Agilent 1100 HPLC-MSD SL quadrapole mass spectrometer connected to a UV/Vis diode array detector. For LC-MS analysis, quenched reaction mixtures were analyzed by analytical reverse-phase HPLC with a 250 mm×4.6 mm Gemini 5µ C18 column (Phenomenex, Torrance, Calif.) using a gradient of 10-90% $CH_3CN$ in 0.1% formic acid/$H_2O$ in 20 min at 1 ml/min, with detection at 254 nm. The enzymatic and/or chemical syntheses sugar nucleotides (FIG. 3: 7-9, 11-25) utilized in this study have been previously described. Borisova S A, et al. (2006) *Angew Chem Int Ed Engl* 45: 2748-53; Barton W A, et al. (2002) *Proc Natl Acad Sci USA* 99: 13397-402; Fu X, et al. (2003) *Nat Biotechnol* 21: 1467-9; Zhang C, et al. (2006) *Science* 313: 1291-4; Borisova S A, et al. (2006) *Angew Chem Int Ed Engl* 45: 2748-53; Jiang J, et al. (2001) *Angew Chem Int Ed Engl* 40: 1502-1505; Losey H C, et al. (2002) *Chem Biol* 9: 1305-14. Donors 2, 6, and 10 (FIG. 3) were from Sigma.

Glycosyltransferase Mutant Library Preparation

The random mutant library was prepared via error-prone PCR using the Stratagene GeneMorph II Random Mutagenesis Kit, as described by the manufacturer using varying quantities of pET28/OleD as template. The primers used for amplification of the OleD gene were T7 FOR (5'-TAA TAC GAC TCA CTA TAG GG-3'; SEQ ID NO:3) and T7 REV (5'-GCT AGT TAT TGC TCA GCG G-3'; SEQ ID NO:4). Amplified product was digested with NdeI and HindIII purified by agarose gel electrophoresis (0.8% w/v agarose), extracted using the QIAquick Gel Extraction Kit (QIAgen, Valenica, Calif.), and ligated into similarly treated pET28a. The ligation mixtures were transformed into chemically competent NovaBlue cells and single colonies used to prepare plasmid for DNA sequencing, which revealed that a library made with ~10 ng starting template had the desired mutation rate of 1-2 amino acid mutations per gene product. Subsequently, all the transformants from this library were pooled and cultured overnight. Plasmid was prepared from this culture and used to transform chemical competent E. coli BL21 (DE3)pLysS, which was screened as described below.

Site-Directed Mutagenesis

Site-specific OleD variants were constructed using the Stratagene QuikChange II Site-Directed Mutagenesis Kit, as described by the manufacturer. The amplified plasmid was digested with DpnI and transformed into chemical competent E. coli XL1 Blue. Constructs were confirmed to carry the correct mutation(s) via DNA sequencing.

Screening

Individual colonies were used to inoculate wells of a 96-deep well microtitre plate wherein each well contained 1 ml of LB medium supplemented with 50 micrograms/ml kanamycin. Culture plates were tightly sealed with AeraSeal™ breathable film (Research Products International Corp.). After cell growth at 37° C. for 18 h with shaking at 350 rpm, 100 microliters of each culture was transferred to a fresh deep-well plate containing 1 ml of LB medium supplemented with 50 micrograms/ml kanamycin. The original plate was sealed and stored at 4° C., or a glycerol copy made by mixing 100 microliters of each culture with 100 microliters 50% (v/v) glycerol and storing at −80° C. The freshly inoculated plate was incubated at 37° C. for 2-3 h with shaking at 350 rpm. Expression of the N-terminal $His_6$-tagged OleD was induced at $OD_{600}$ ~0.7, and isopropyl beta-D-thiogalactoside (IPTG) was added to a final concentration of 0.4 mM and the plate incubated for 18 h at 18° C. Cells were harvested by centrifugation at 3000 g for 10 min at 4° C., the cell pellets thoroughly resuspended in chilled 50 mM Tris-HCl (pH 8.0) containing 10 mg/ml lysozyme (Sigma), and the plates were subjected to a single freeze/thaw cycle to lyse the cells. Following thawing, cell debris was collected by centrifugation at 3000 g for 20 min at 4° C. and 50 microliters of the cleared supernatant used for enzyme assay.

For the assay, cleared supernatant was mixed with an equal volume (50 microliters) of 50 mM Tris-HCl (pH 8.0) containing 10 mM $MgCl_2$, 0.2 mM 4-Me-umb (FIG. 1: 4), and 1.0 mM UPDG (FIG. 3: 2) using a Biomek FX Liquid Handling Workstation (Beckman Coulter, Fullerton, Calif.). Upon mixing, the fluorescence at excitation 350 nm and emission 460 nm was measured using a FLUOstar Optima plate reader (BMG Labtechnologies, Durham, N.C.) and the reactions incubated for 4 h at 30° C., at which time the fluorescence measurement was repeated. Activity of the clones was expressed as the difference in fluorescence intensity between 0 h and 3 h.

Protein Expression and Purification

For characterization of specific OleD variants, single colonies were used to inoculate 3 ml LB medium supplemented with 50 micrograms/ml kanamycin and cultured overnight at 37° C. The entire starter culture was then transferred to 1 liter LB medium supplemented with 50 micrograms/ml kanamycin and grown at 37° C. until the $OD_{600}$ was ~0.7, then IPTG to a final concentration of 0.4 mM was added and the flask incubated for 18 h at 18° C. Cell pellets were collected by centrifugation at 10,000 g and 4° C. for 20 min, resuspended into 10 ml 20 mM phosphate buffer, pH 7.4, containing 0.5M NaCl and 10 mM imidazole and were lysed by sonication. Cell debris was removed by centrifugation at 10,000 g and 4° C. for 30 min and the cleared supernatant immediately applied to 2 ml of nickel-nitrilotriacetic acid (Ni-NTA) resin (QIAgen Valencia, Calif.), pre-equilibrated with the lysis buffer. Protein was allowed to bind for 30 min at 4° C. with gentle agitation, and the resin washed 4 times with 50 ml each lysis buffer. Finally, the enzyme was eluted by incubation of the resin with 2 ml lysis buffer containing 100 mM imidazole for 10 min at 4° C. with gentle agitation. The purified enzyme was applied to a PD-10 desalting column (Amersham Biosciences AB) equilibrated with 50 mM Tris-HCl (pH 8.0) and eluted as described by the manufacturer. Protein aliquots were immediately flash frozen in liquid nitrogen and stored at −80° C. Protein purity was verified by SDS-PAGE. Protein quantification was carried out using the Bradford Protein Assay Kit from Bio-Rad.

It should be noted that the above description, attached materials and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments. All publications, references to deposited sequences, patents and patent applications cited herein are hereby incorporated by reference in their entirety for all purposes.

What is claimed is:

1. An isolated mutant glycosyltransferase comprising:
   (a) the amino acid sequence of OleD glycosyltransferase set forth in SEQ ID NO: 1, wherein proline at position 67 has been replaced with threonine, serine at position 132 has been replaced with phenylalanine, alanine at position 242 has been replaced with leucine, and glutamine at position 268 has been replaced with valine; or
   (b) an amino acid sequence which has at least 95% sequence identity to SEQ ID NO:1, wherein the proline at position 67 has been replaced with threonine, the serine at position 132 has been replaced with phenylalanine, the alanine at position 242 has been replaced with leucine, and the glutamine at position 268 has been replaced with valine, wherein said isolated mutant exhibits an improved conversion of nucleotide diphosphate (NDP) to NDP sugar as compared to a corresponding non-mutated glycosyltransferase.

2. The isolated mutant glycosyltransferase according to claim 1, wherein said isolated mutant glycosyltransferase is encoded by a nucleotide that hybridizes under stringent conditions 4× sodium chlorine/sodium citrate (SSC), at about 65-70° C. (or hybridization in 4×SSC plus 50% formamide at about 42-50° C.) followed by one or more washes in 1×SSC, at about 65-70° C. to the nucleotide sequence set forth in SEQ ID NO:2.

* * * * *

SEQUENCE LISTING

```
<160> NUMBER OF SEQ ID NOS: 2

<210> SEQ ID NO 1
<211> LENGTH: 415
<212> TYPE: PRT
<213> ORGANISM: Streptomyces antibioticus

<400> SEQUENCE: 1

Met Thr Thr Gln Thr Thr Pro Ala His Ile Ala Met Phe Ser Ile Ala
1               5                   10                  15
```

-continued

```
Ala His Gly His Val Asn Pro Ser Leu Glu Val Ile Arg Glu Leu Val
         20                  25                  30

Ala Arg Gly His Arg Val Thr Tyr Ala Ile Pro Pro Val Phe Ala Asp
         35                  40                  45

Lys Val Ala Ala Thr Gly Ala Arg Pro Val Leu Tyr His Ser Thr Leu
 50                  55                  60

Pro Gly Pro Asp Ala Asp Pro Glu Ala Trp Gly Ser Thr Leu Leu Asp
 65                  70                  75                  80

Asn Val Glu Pro Phe Leu Asn Asp Ala Ile Gln Ala Leu Pro Gln Leu
                 85                  90                  95

Ala Asp Ala Tyr Ala Asp Asp Ile Pro Asp Leu Val Leu His Asp Ile
            100                 105                 110

Thr Ser Tyr Pro Ala Arg Val Leu Ala Arg Arg Trp Gly Val Pro Ala
            115                 120                 125

Val Ser Leu Ser Pro Asn Leu Val Ala Trp Lys Gly Tyr Glu Glu Glu
        130                 135                 140

Val Ala Glu Pro Met Trp Arg Glu Pro Arg Gln Thr Glu Arg Gly Arg
145                 150                 155                 160

Ala Tyr Tyr Ala Arg Phe Glu Ala Trp Leu Lys Glu Asn Gly Ile Thr
                165                 170                 175

Glu His Pro Asp Thr Phe Ala Ser His Pro Pro Arg Ser Leu Val Leu
            180                 185                 190

Ile Pro Lys Ala Leu Gln Pro His Ala Asp Arg Val Asp Glu Asp Val
            195                 200                 205

Tyr Thr Phe Val Gly Ala Cys Gln Gly Asp Arg Ala Glu Glu Gly Gly
        210                 215                 220

Trp Gln Arg Pro Ala Gly Ala Glu Lys Val Val Leu Val Ser Leu Gly
225                 230                 235                 240

Ser Ala Phe Thr Lys Gln Pro Ala Phe Tyr Arg Glu Cys Val Arg Ala
                245                 250                 255

Phe Gly Asn Leu Pro Gly Trp His Leu Val Leu Gln Ile Gly Arg Lys
            260                 265                 270

Val Thr Pro Ala Glu Leu Gly Glu Leu Pro Asp Asn Val Glu Val His
            275                 280                 285

Asp Trp Val Pro Gln Leu Ala Ile Leu Arg Gln Ala Asp Leu Phe Val
        290                 295                 300

Thr His Ala Gly Ala Gly Gly Ser Gln Glu Gly Leu Ala Thr Ala Thr
305                 310                 315                 320

Pro Met Ile Ala Val Pro Gln Ala Val Asp Gln Phe Gly Asn Ala Asp
                325                 330                 335

Met Leu Gln Gly Leu Gly Val Ala Arg Lys Leu Ala Thr Glu Glu Ala
            340                 345                 350

Thr Ala Asp Leu Leu Arg Glu Thr Ala Leu Ala Leu Val Asp Asp Pro
            355                 360                 365

Glu Val Ala Arg Arg Leu Arg Arg Ile Gln Ala Glu Met Ala Gln Glu
        370                 375                 380

Gly Gly Thr Arg Arg Ala Ala Asp Leu Ile Glu Ala Glu Leu Pro Ala
385                 390                 395                 400

Arg His Glu Arg Gln Glu Pro Val Gly Asp Arg Pro Asn Gly Gly
                405                 410                 415
```

<210> SEQ ID NO 2
<211> LENGTH: 1248
<212> TYPE: DNA
<213> ORGANISM: Streptomyces antibioticus

<400> SEQUENCE: 2

```
atgaccaccc agaccactcc cgcccacatc gccatgttct ccatcgccgc ccacggccat    60
gtgaacccca gcctggaggt gatccgtgaa ctcgtcgccc gcggccaccg ggtcacgtac   120
gccattccgc ccgtcttcgc cgacaaggtg gccgccaccg gcgcccggcc cgtcctctac   180
cactccaccc tgcccggccc cgacgccgac ccggaggcat ggggaagcac cctgctggac   240
aacgtcgaac cgttcctgaa cgacgcgatc caggcgctcc cgcagctcgc cgatgcctac   300
gccgacgaca tccccgatct cgtcctgcac gacatcacct cctacccggc ccgcgtcctg   360
gcccgccgct ggggcgtccc ggcggtctcc ctctccccga acctcgtcgc ctggaagggt   420
tacgaggagg aggtcgccga gccgatgtgg cgcgaacccc ggcagaccga gcgcggacgg   480
gcctactacg cccggttcga ggcatggctg aaggagaacg ggatcaccga gcacccggac   540
acgttcgcca gtcatccgcc gcgctccctg gtgctcatcc cgaaggcgct ccagccgcac   600
gccgaccggg tggacgaaga cgtgtacacc ttcgtcggcg cctgccaggg agaccgcgcc   660
gaggaaggcg gctggcagcg gcccgccggc gcggagaagg tcgtcctggt gtcgctcggc   720
tcggcgttca ccaagcagcc cgccttctac cgggagtgcg tgcgcgcctt cgggaacctg   780
cccggctggc acctcgtcct ccagatcggc cggaaggtga ccccgccga actgggggag   840
ctgccggaca acgtggaggt gcacgactgg gtgccgcagc tcgcgatcct gcgccaggcc   900
gatctgttcg tcacccacgc gggcgccggc ggcagccagg aggggctggc caccgcgacg   960
cccatgatcg ccgtaccgca ggccgtcgac cagttcggca acgccgacat gctccaaggg  1020
ctcggcgtcg cccggaagct ggcgaccgag gaggccaccg ccgacctgct ccgcgagacc  1080
gccctcgctc tggtggacga cccggaggtc gcgcgccggc tccggcggat ccaggcggag  1140
atggcccagg agggcggcac ccggcgggcg gccgacctca tcgaggccga actgcccgcg  1200
cgccacgagc ggcaggagcc ggtgggcgac cgacccaacg gtgggtga              1248
```